US009256713B2

(12) United States Patent
March et al.

(10) Patent No.: US 9,256,713 B2
(45) Date of Patent: *Feb. 9, 2016

(54) LIBRARY GENERATION FOR DETECTION AND IDENTIFICATION OF SHIELDED RADIOISOTOPES

(75) Inventors: Don Daniel March, Alexandria, VA (US); Anthony Bresenhan Kaye, Fairfax, VA (US)

(73) Assignee: Exelis Inc., Herndon, VA (US)

( * ) Notice: Subject to any disclaimer, the term of this patent is extended or adjusted under 35 U.S.C. 154(b) by 1567 days.

This patent is subject to a terminal disclaimer.

(21) Appl. No.: 12/106,385

(22) Filed: Apr. 21, 2008

(65) Prior Publication Data

US 2009/0265386 A1    Oct. 22, 2009

(51) Int. Cl.
| | |
|---|---|
| *G01N 33/48* | (2006.01) |
| *G06G 7/48* | (2006.01) |
| *G06F 19/00* | (2011.01) |
| *G06F 19/24* | (2011.01) |
| *G06F 19/12* | (2011.01) |

(Continued)

(52) U.S. Cl.
CPC ............... *G06F 19/707* (2013.01); *G01T 1/00* (2013.01); *G01V 5/0008* (2013.01); *G06F 19/12* (2013.01); *G06F 19/24* (2013.01); *G06F 19/26* (2013.01); *G06F 19/705* (2013.01); *G06F 19/709* (2013.01)

(58) Field of Classification Search
None
See application file for complete search history.

(56) References Cited

U.S. PATENT DOCUMENTS

| 5,369,578 A | 11/1994 | Roscoe et al. | |
|---|---|---|---|
| 8,463,556 B2 * | 6/2013 | Kaye | ............................... 702/22 |

(Continued)

FOREIGN PATENT DOCUMENTS

| JP | 2009524161 | 6/2009 |
|---|---|---|
| WO | 2007065004 A2 | 6/2007 |

OTHER PUBLICATIONS

Zhao et al. X-ray imaging using amorphous selenium: Feasibility of a flat panel self-scanned detector for digital radiology. Medical Physics, vol. 22, 1995, pp. 1595-1604.*

(Continued)

*Primary Examiner* — Russell S Negin
(74) *Attorney, Agent, or Firm* — Edell, Shapiro & Finnan LLC

(57) ABSTRACT

A method, logic and system are provided for generating data representing all possible materials that may be present when monitoring a region or space for a radioisotope of interest. All possible materials with which a radioisotope material may interact are grouped or categorized into one of a plurality of material groups. Each material group is further subdivided into a plurality of subgroups based on atomic number of a material. First data is stored for each of the subgroups of each of the plurality of material groups, where the first data represents an interaction between a representative material for a corresponding subgroup and radiation at a plurality of energy levels. Second data is stored representing spectral characteristics of each radioisotope of interest at the plurality of energy levels. For a radioisotope of interest, a computation is made to produce spectrum data resulting from an interaction between of the radioisotope of interest using the second data with the first data for each of the plurality of subgroups in each material group. The spectrum data is then stored in a library for later use in the field with the output from a detector. Spectrum data is stored for the particular detector to be used in the field, and to this end, such detector-specific spectrum library data may be adjusted to account for a detector's quantum efficiency and resolution characteristics.

25 Claims, 4 Drawing Sheets

(51) Int. Cl.
*G06F 19/26* (2011.01)
*G01T 1/00* (2006.01)
*G01V 5/00* (2006.01)

(56) References Cited

U.S. PATENT DOCUMENTS

2010/0137148 A1* 6/2010 Kaye ................................ 506/8
2010/0305873 A1* 12/2010 Sjoden et al. .................... 702/30

OTHER PUBLICATIONS

Victor Orphan, et al., "Advanced Cargo Container Scanning Technology Development," Science Applications International Corporation, San Diego, California 92127, 7th Marine Transportation System Research and Technology Conference, Washington, D.C., Nov. 16-17, 2004.
Berkeley Nucleonics Corporation (BNC), Model 1703MB/GNB Gamma/Gamma-Neutron Pager, Product Information Brochure, Jan. 2007.
Extended Search Report and Written Opinion in counterpart European Application No. 09157904, dated Oct. 30, 2009.
Katja Roemer et al., "Simulation of Template Spectra for Scintillator Based Radionuclide Identification Devices Using GEANT4," IEEE Nuclear Science Symposium Conference Record, 2006; Nuclear Science Symposium, Medical Imaging Conference, 15th International Workshop on Room Temperature Semiconductor X- and Gamma-Ray Detectors; Oct. 29-Nov. 4, 2006, San Diego, California, vol. 1, Oct. 29, 2006, pp. 247-252, XP002509029.
Will H. Hill et al., "Experimental Verification of a Hand Held Electronically-Collimated Radiation Detector," Nuclear Science Symposium Conference Record, 2007; NSS '07; IEEE, IEEE, PI, Oct. 1, 2007, pp. 3792-3797, XP031206432.
S. Agostinelli et al., "GEANT4—a simulation toolkit," Nuclear Instruments and Methods in Physics Research, Section—A: Accelerators, Spectrometers, Detectors and Associated Equipment, Elsevier, Amsterdam, NL, vol. 506, No. 3, Jul. 1, 2003, pp. 250-303, XP004431463.
A. L. Nichols, "Decay Data: Review of Measurements, Evaluations and Compilations," Applied Radiation and Isotopes, Elsevier, Oxford, GB, vol. 55, No. 1, Jul. 1, 2001, pp. 23-70, XP004234045.
R. E. Abdel-Aal et al., "Determination of Radioisotopes in Gamma-Ray Spectroscopy Using Abductive Machine Learning," Nuclear Instruments & Methods in Physics Research, Section—A: Accelerators, Spectrometers, Detectors and Associated Equipment, Elsevier, Amsterdam, NL, vol. 391, No. 2, Jun. 1, 1997, pp. 275-288, XP004084518.
R. J. Estep et al., "The Multiple Isotope Material Basis Set (MIMBS) Method for Isotope Identification with Low- and Medium-Resolution Gamma-Ray Detectors," Journal of Radioanalytical and Nuclear Chemistry, vol. 276, No. 3, May 2, 2008, pp. 737-741.
R. P. Gardner et al., "Status of Software for PGNAA Bulk Analysis by the Monte Carlo—Library Least-Squares (MCLLS) Approach," Journal of Radioanalytical and Nuclear Chemistry, vol. 264, No. 1, Mar. 1, 2005, pp. 221-228.
M. Magistris et al., "The Fingerprint Method for Characterization of Radioactive Waste in Hadron Accelerators," Nuclear Instruments and Methods in Physics Research, Section—A: Accelerators, Spectrometers, Detectors and Associated Equipment, Elsevier, Amsterdam, NL, vol. 591, No. 2, Jun. 21, 2008, pp. 343-352.
English translation of Office Action in corresponding Japanese Patent Application No. 2009-095361, dated Aug. 16, 2012.

* cited by examiner

LIBRARY GENERATION FOR DETECTION AND IDENTIFICATION OF SHIELDED RADIOISOTOPES

CROSS REFERENCE TO RELATED APPLICATIONS

The present is related to commonly assigned and co-pending U.S. application Ser. No. 11/847,602, filed Aug. 30, 2007, entitled "System and Method for Radioisotope Identification", the entirety of which is incorporated herein by reference.

BACKGROUND

Efforts are underway to develop technologies capable of detecting the presence of materials that may be placed inside a container for purposes of transporting the material to a destination. Examples of harmful materials that may be most important to identify are radioactive, explosive, biological, and/or chemical agents.

Current radioisotopic identification is based upon peak-finding and pattern-matching algorithms. These techniques may be sufficient in the laboratory and in some industrial applications (e.g., in commercial nuclear power reactors), but they fall short in attempts to detect shielded radioisotopes, largely because current algorithms do not sufficiently account for the interaction between the emitted radiation and the surrounding matter.

The aforementioned co-pending application presents a system and method for modeling the interaction of radioisotope materials with any shielding material in order to rapidly analyze output of a detector to determine whether a radioisotope material of interest is present in a field of view of the detector. There is room for improving on those techniques, and in particular, for building a reliable library of data representing interactions between radioisotopes of interest and possible materials in any combination.

SUMMARY

Briefly, a method, computer software and system are provided for generating data representing all possible materials that may be present when monitoring a region or space for a radioisotope of interest. All possible materials with which a radioisotope material may interact are grouped or categorized into one of a plurality of material groups. Each material group is further subdivided into a plurality of subgroups based on the atomic number and/or the electron affinity of a material. First data is stored for each of the subgroups of each of the plurality of material groups, where the first data represents an interaction between a representative material for a corresponding subgroup and radiation at a plurality of energy levels. Second data is stored representing spectral characteristics of each radioisotope of interest at the plurality of energy levels. For a radioisotope of interest, a computation is made to produce spectrum data resulting from an interaction between of the radioisotope of interest using the second data with the first data for each of the plurality of subgroups in each material group. The spectrum data is then stored in a library for later use in the field with the output from a detector. Spectrum data is stored for the particular detector to be used in the field, and to this end, such detector-specific spectrum library data may be adjusted to account for a detector's quantum efficiency and resolution characteristics.

DETAILED DESCRIPTION

Figure 1:
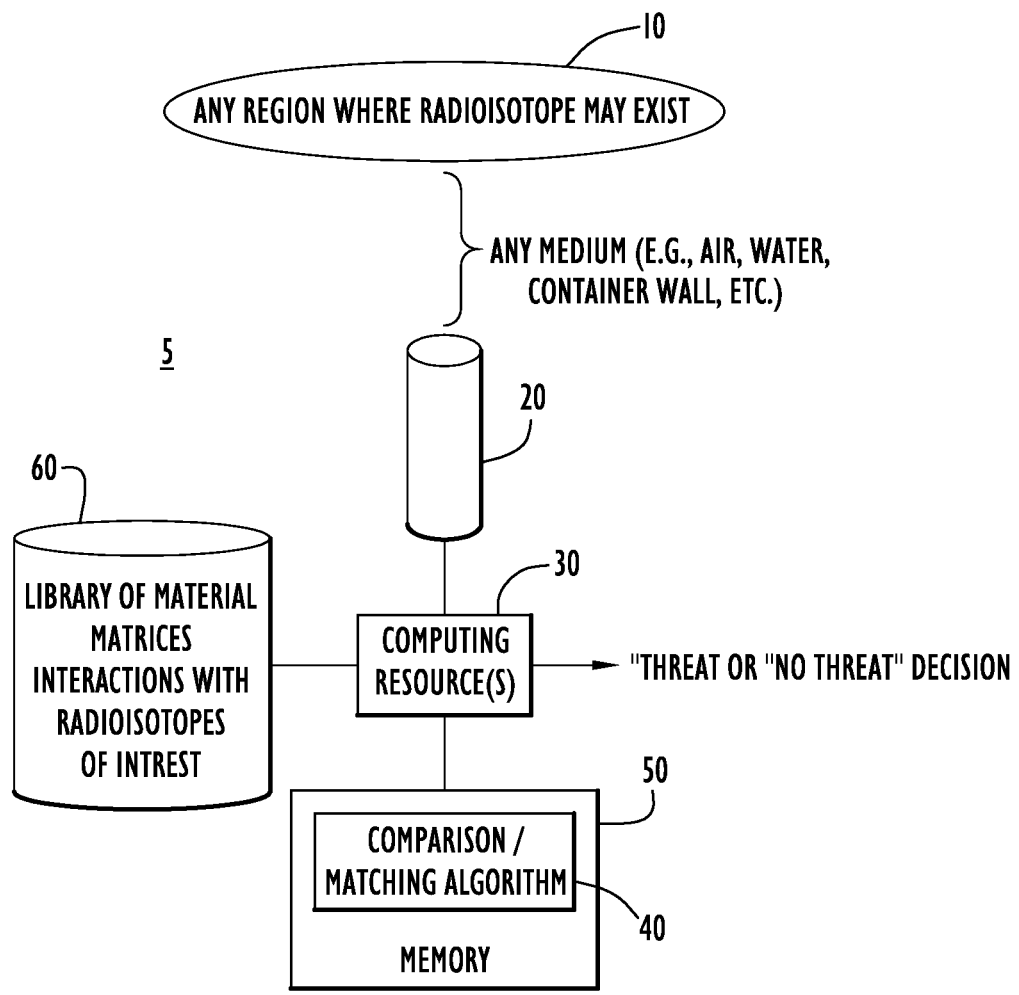
FIG. 1 is an example of a block diagram of a detection system for detecting the presence of a radioisotope material.

Referring first to FIG. 1, a block diagram is shown of a system 5 that is useful to detect the presence of and identify a radioisotope material of interest that in any region or space 10. A detector 20 interrogates the region or space 10 for spectral signatures associated with a radioisotope material of interest. In general, the detector 20 may be any detector or detection system that produces spectra.

The region or space 10 may be any open or closed space, including, but not limited to small containers, large containers (such as cargo shipping containers), luggage, vehicles, handbags, backpacks, clothing, etc. The region 10 may be stationary or in motion.

Computing resources 30, coupled to receive the output of the detector 20, analyzes the detector output by executing computer software instructions for a comparison or matching algorithm 40 stored in a computer readable memory 50. The memory 50 may be random access memory (RAM), read only memory (ROM), a combination thereof, or any other type of suitable computer readable memory. In one example, the memory 50 may reside within the computing resources 30 (as is the case with a desktop computer). However, it is also possible that the memory 50, containing the program for the comparison algorithm 40, be accessible by the computing resources 30 through a wired or wireless connection (network or dedicated) so that the computing resources 30 remain connected to the detector 20. When performing the comparison algorithm 40, the computer resources 30 refers to a data library 60 that contains data representing mathematical modeled physical interactions between one or more radioisotope materials of interest with data for all possible materials of interest that could be present between the face of the detector 20 and a radioisotope of interest. The ability to simplify the generation of the data in the library 60 is desirable in order to provide for a more reliable and practically useful system 5. The comparison/matching algorithm 40 is not limited to use with any particular form or type of detector 20 as long as the detector produces a spectrum (i.e., energy level versus frequency or energy level versus wavelength) of some sort as output; nevertheless, examples of such detectors 20 are those based upon semiconductor technology (including but not limited to: silicon detectors, diamond detectors, germanium detectors, cadmium-telluride detectors, mercuric iodide detectors, cadmium zinc telluride detectors, thorium tetraboride detectors, lanthaide or actinide halide detectors), scintillator technology (including but not limited to: alkali halides (including sodium iodide), slow organic scintillators (e.g., zinc sulfide), unactivated fast inorganic scintillators (e.g., cesium iodide), cerium-activated fast inorganic scintillators (e.g., cerium-doped yttrium aluminum garnet or YAG:Ce), and glass scintillators (e.g., cerium-activated lithium glass), or any derivative thereof, or those based on physical "gating" or time-of-flight.

To this end, techniques are provided to reduce the complexity in generating and amount of data needed for use in the data library 60. As a foundation for the techniques described herein, reference is now made to FIG. 2 for the following discussion.

Figure 2:
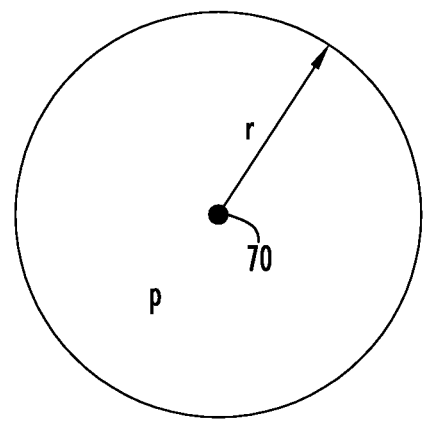
FIG. 2 illustrates an example of a simple radiation transport arrangement.

FIG. 2 illustrates a radiation transport problem in which there is a mono-energetic point photon source of energy $E_i$ at the center shown at 70 of a sphere of a single, uniform material having radius r and density ρ. In computing the transport of the photons, the results are tallied on the exterior surface of the sphere, at r.

Radiation interacts with matter in a well-known way. The intensity of radiation, I, from a monochromatic photon source along any given path as a fraction of its original intensity, $I_0$, is given by the relationship:

$$\frac{I}{I_0} = e^{-\rho\sigma x},$$

in which the particles (in the context of the present invention, either photons or neutrons) travel through a single material, having a density ρ, a total cross section for interaction G (that depends not only upon the specific particle, but on the energy E of the particle when it interacts with the material), and the path length x through which the particle travels. A more generalized relationship can be written for interaction with multiple materials. Therefore, as radiation travels through various materials (including air), the detected spectrum (signature) is likely to be weakened (reduced in amplitude) and the various peaks in the spectrum are likely to be shifted in energy. Each spectral feature may be affected differently from the rest. The identification of specific radioisotopes is not only a matter of signal-to-noise conditions, but also involves understanding, modeling, and coding the interaction of radiation with matter in a way from which the end user will benefit.

While these various interactions are, by and large, understood and can be modeled and predicted very well (using, e.g., Monte Carlo computer software known in the art as "MCNP" or "PENELOPE"), they require that the entire geometry (including material properties) be specified. Once the geometry is defined, these software algorithms use Monte Carlo techniques and massive cross-section libraries (e.g., the "ENDF-VI" libraries distributed by, e.g., the National Nuclear Data Center, the Radiation Safety Information Computational Center, and the Nuclear Reaction Data Centers; the libraries can require the use of large amounts of computer storage space) to simulate the specified problem. If all of the materials, their physical properties (e.g., density) and specific chemical compositions, and their respective location(s) and geometric configuration(s) in the problem are not well defined, these software algorithms become less than optimal.

When the radius r and the density ρ are each set to a very small constant value, and the initial photon energy is allowed to range among a plurality of energy levels from $E_1$ to $E_n$, then each of the resulting spectra form a column vector $\vec{E}_i$ of a material matrix M. The material matrix M is square because the number of column vectors and the number of energy bins are both identically n:

$$M = \begin{bmatrix} E_{1,1} & E_{1,2} & E_{i,j} \dots & E_{1,n} \\ E_{2,1} & E_{2,2} & & E_{2,n} \\ \dots & & & \dots \\ \dots & & \dots & E_{n,n} \end{bmatrix},\quad (1)$$

in which $E_{i,j}$ represents the Monte Carlo Neutron and Photon (MCNP)-calculated value (i.e., tally) resulting from transport of a mono-energetic source of energy $E_i$ through the material. Thus, each column of the matrix represents resulting spectra at a plurality of energy levels $E_1$ to $E_n$. The matrix M has the property that it accurately represents the interaction between radiation and a chosen material at all energies of interest. As a result, all of the transport physics associated with the interaction is summarized in a single matrix. In one example, the x-ray spectrum (where radioisotope radiation is of concern or interest) is divided into a very large number of finely-spaced bins or levels, where the lowest bin energy is 10 keV and the highest bin energy is 2.6 MeV.

The matrix M does not contain any information about radioisotopes of interest. Accordingly, a column vector is defined that is populated with the normalized in vaccuo spectrum of a radioisotope of interest (without self-shielding) for each energy level $E_i$. This vector, referred to herein as an isotope vector, $\vec{\beta}$, expressed as:

$$\vec{\beta} = \begin{bmatrix} a_1 \\ a_2 \\ \dots \\ a_n \end{bmatrix},\quad (3)$$

where $a_1, a_2, \dots, a_n$ are the spectrum amplitudes in energy bins $E_1, \dots, E_n$, respectively.

Thus, the interaction between a material an a radioisotope is computed by the following matrix-vector multiplication:

$$P = M\vec{\beta} \quad (3)$$

$$= \begin{bmatrix} E_{1,1} & E_{1,2} & E_{i,j} \dots & E_{1,n} \\ E_{2,1} & E_{2,2} & & E_{2,n} \\ & & & \dots \\ \dots & & \dots & E_{n,n} \end{bmatrix} \begin{bmatrix} a_1 \\ a_2 \\ \dots \\ a_n \end{bmatrix},\quad (4)$$

in which P is the resulting spectrum.

As noted above, arbitrarily small values for ρ and r were selected to generative the matrix M in equation 1. In order to consider as many combinations of density and path lengths as possible, these to parameters are combined to form a single scalar density-path length quantity, Γ:

$$\Gamma = \alpha \rho r, \quad (5)$$

in which α is a normalization constant and is always a non-negative integer. Using this construct, many values of ρ and r can be achieved, and in fact, all of the physically plausible values can be found since the difference between any two values is very small. (This is because of the initial values of ρ and r and the condition that each could be arbitrary, but very small.) The interaction of a single material of any density ρ and any thickness r and a single radioisotope material can be represented as:

$$P = M^\Gamma \vec{\beta}. \quad (6)$$

When Γ=0, M becomes the identity matrix and $P = \vec{\beta}$.

For some applications, the density/path-length term Γ may be varied over a range from 0 to some maximum value in integer increments so as to produce a different matrix M for each value of Γ in order to accommodate modeling of thicker materials.

Figure 3:
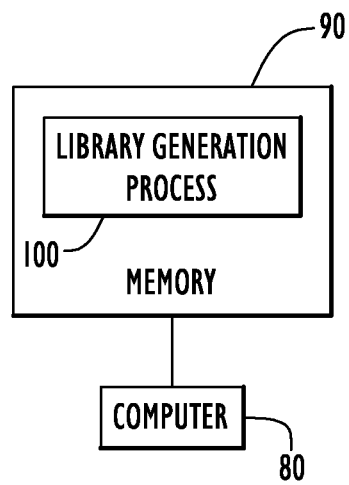
FIG. 3 is an example of a block diagram of a system configured to generate a library of data representing the interaction of materials with radioisotopes of interest.

FIG. 3 shows an example of an arrangement for generating the library 60. A computer (or multiple computers) 80 is provided that executes one or more software programs stored in a memory 90. In particular, the memory 90 stores computer program instructions for a library generation process shown at 100. The memory 90 is any computer readable medium that is capable of storing instructions (as well as data). More generally, the library generation process 100 (and the comparison/matching algorithm 40 referred to above in FIG. 1) may be implemented by logic encoded in one or more tangible media (e.g., embedded logic such as an application specific integrated circuit, digital signal processor firmware instructions, software that is executed by a processor, etc.).

Figure 4:
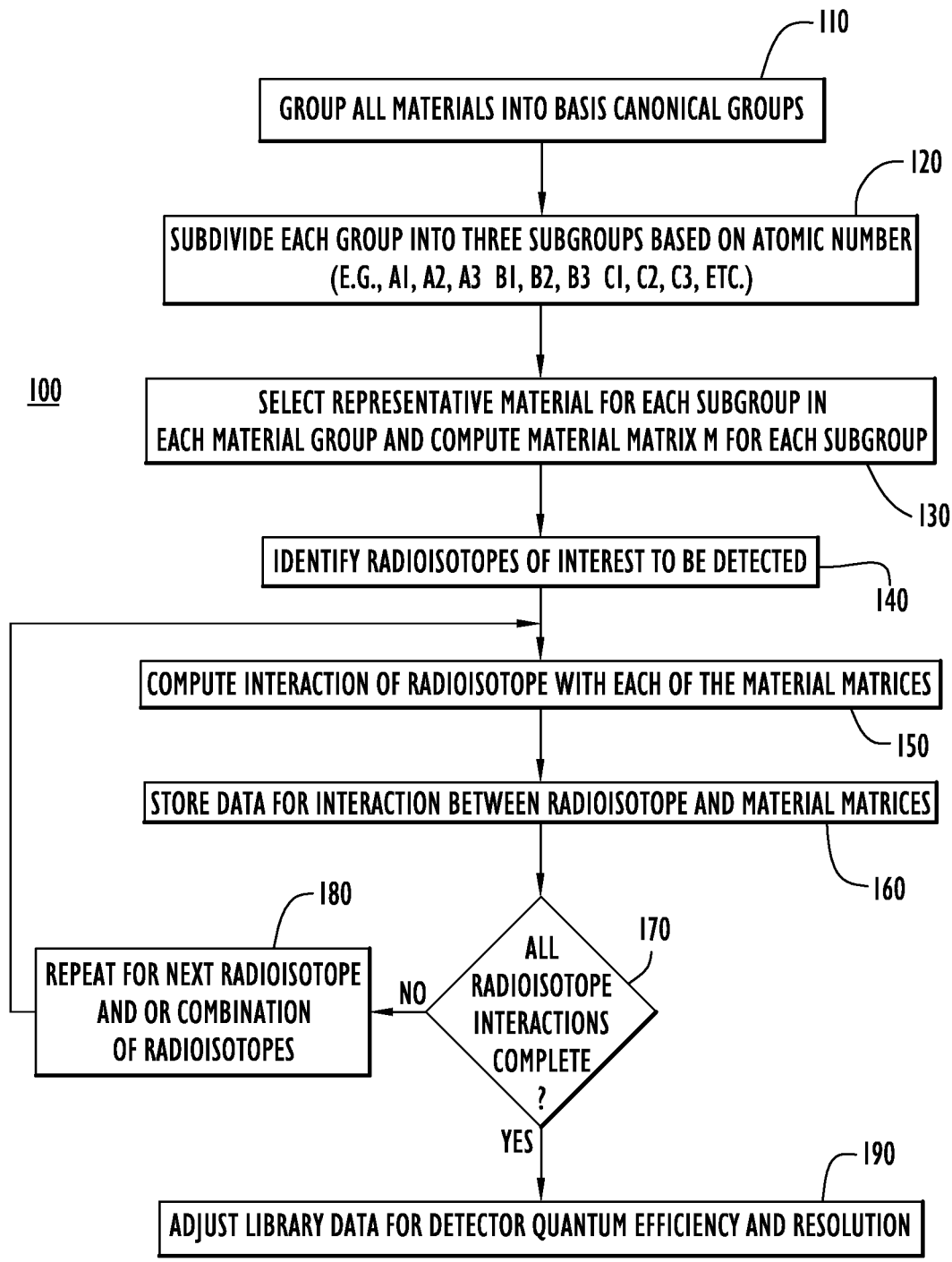
FIG. 4 is an example of a flow chart of a library generation process that generates the data representing the interaction of materials with radioisotopes of interest.

Turning now to FIG. 4, an example of a flow chart depicting execution of the library generation process 100 is now described. At 110, all possible materials heretofore known (or hereinafter discovered) that exist are grouped into one of a plurality of material groups. For example, there are a number of basic material groups (e.g., plastics, ceramics, metals, etc.). Next, at 120, each material group is subdivided into a plurality of subgroups based on atomic number (Z) or electron affinity, in which a first subgroup is for materials having a low atomic number, a second subgroup is for materials having a moderate atomic number, and a third subgroup is for materials having a high atomic number. For example, in the metal materials group, there is a low atomic number subgroup (e.g., for materials such as aluminum), a moderate atomic number subgroup (e.g., for materials such as stainless steel) and a high atomic number subgroup (e.g., for materials such as gadolinium).

As shown at 120 in FIG. 4, the following notation is adopted for simplicity:

Each of the material groups is represented by the letters A, B, and C, but it is to be understood that this is only an example and that there may be more or less than three material groups.

Each of the subgroups or categories within the material groups that represent the low, moderate, and high atomic number representative materials within the material group is given an integer subscript to the material group notation: e.g., $A_1$, $A_2$, $A_3$, where $A_1$ denotes the low atomic number subgroup of material group A, $A_2$ denotes the moderate-atomic number subgroup in material group A, and $A_3$ represents the high-atomic number subgroup in material group A, and so on for the other material groups.

Virtually all materials can be accurately represented by one of the combinations of material groups and subgroups (categories) set forth above. Each material group and subgroup can be represented by their own respective material matrix, M.

At 130, a representative material is selected for each subgroup in each material group and using that selected material together with known MCNP values for the material, the individual column vectors for the material matrix M that represents that subgroup is computed.

At 140, the one or more radioisotopes of interests whose presence is to be detected and identity confirmed are identified for purposes of computing the interaction data that is stored in the library. Although it is certainly possible, for many applications it may not be necessary to model all known radioisotopes, of which there are currently approximately 3,800. It may be desirable to be concerned only with those radioisotopes that are present a potential radiological or nuclear threat to animal and/or plant life, or those that have a certain half-life.

At 150, the interaction of a radioisotope of interest with each material matrix M for all subgroups is computed. However, as would be appreciated by those in the art, generally speaking the interaction of a single radioisotope with a single material is not necessarily very interesting or useful.

As explained above in connection the material groups and subgroups at 110 and 120, the materials "world" can be modeled quite accurately (in the x-ray regime) using three representative materials from the selected number of canonical groups. For the sake of simplifying notation, this entire collection of materials is referred to as K:

$$\kappa \equiv \{A_1, A_2, A_3, B_1, \ldots, C_3\} \quad (7)$$

The interaction of a single radioisotope with these materials is then:

$$P = \prod_{j \in \kappa} M_j^{\Gamma_j} \vec{\beta}. \quad (8)$$

For some detection applications, the ordering of the material matrices $M_j$ is not relevant because it may be assumed that the matrices $M_j$ commute. The value of $\Gamma$ associated with each matrix $M_j$ is therefore the sum of all of the individual values of $\Gamma$ for each element of $\kappa_j$. On the other hand, there may be applications where the assumption that the matrices commute does not hold and in that case the ordering of the matrices would need to be accounted for in addition to the value of $\Gamma$, which would increase the amount of computations needed.

Materials containing more than one radioisotope (so-called "blended sources") can be modeled simply by normalizing the ratio of the individual spectral line strengths and scaling them appropriately in $\vec{\beta}$.

When there are multiple radioisotope sources to be considered in building the library, equation 8 can be expanded to a series of simple linear combinations. For J radioisotope sources, equation 8 becomes:

$$P = \delta_1 \prod_{j \in \kappa} M_j^{\Gamma_j} \vec{\beta}_1 + \delta_2 \prod_{j \in \kappa} M_j^{\Gamma_j} \vec{\beta}_2 + \ldots, \delta_J \prod_{j \in \kappa} M_j^{\Gamma_j} \vec{\beta}_J. \quad (9)$$

$$= \sum_{i=1}^{J} \delta_i \prod_{j \in \kappa} M_j^{\Gamma_j} \vec{\beta}_i, \quad (10)$$

in which $\delta_i$ is the weighted fraction of the radiation by each of the individual J radioisotope sources modeled as $\vec{\beta}_i$.

After the interaction between the radioisotopes of interest and the materials of interest are computed at 150, the resulting interaction data is stored (in the library 60—FIG. 1). As shown at 170 and 180, the computations at 150 and storing at 160 is repeated for all of the radioisotopes and combinations thereof of interest. The interaction data that represents the spectrum that would be produced by a detector if the one or more radioisotopes considered in the interaction data were present together with any one or more of the representative materials in any combination, but not accounting for detector quantum efficiency (DQE) and detector resolution, described hereinafter.

There are characteristics of the particular detector that may be used in the field that may have in impact on the comparison of real-time generated spectra with the spectra in the library. Two such characteristics are the DQE and detector resolution.

Generally, DQE is unique for each detector make and model. DQE information is also relatively easily obtained because the manufacturer of the detector typically provides DQE information in the specifications for its detector products. The DQE can be represented as a matrix with scalar values [0,1] along the main diagonal, that is, a single scalier multiplier μ for each energy level $E_i$. All off-diagonal values of this matrix are identically zero. Adjustment to the spectrum data P can be made "after the fact" when the P computations have already been made, such that:

$$S = DP \tag{11}$$

$$= \begin{bmatrix} \mu_1 & 0 & 0 & \ldots & 0 \\ 0 & \mu_2 & & & 0 \\ 0 & 0 & \ldots & \mu_3 & \ldots & \ldots \\ \ldots & & & & \ldots & \mu_n \end{bmatrix} \sum_{i=1}^{J} \delta_i \prod_{j \in \kappa} M_j^{\Gamma_j} \vec{\beta}_i, \tag{12}$$

in which S is the spectrum data after adjusted by the DQE matrix D.

The resolution of a detector device also affects the information analyzes for presentation for a user. Depending on the energy bin resolution chosen, it may be desirable to make a resolution correction by co-adding collections of energy bins ($E_i$) in the material matrices M, the spectrum data P and/or the DQE adjusted spectrum data S to match the specifications and/or performance measurements for a given detector. In any event, the adjustments for DQE are made before the adjustments for resolution.

Figure 5:
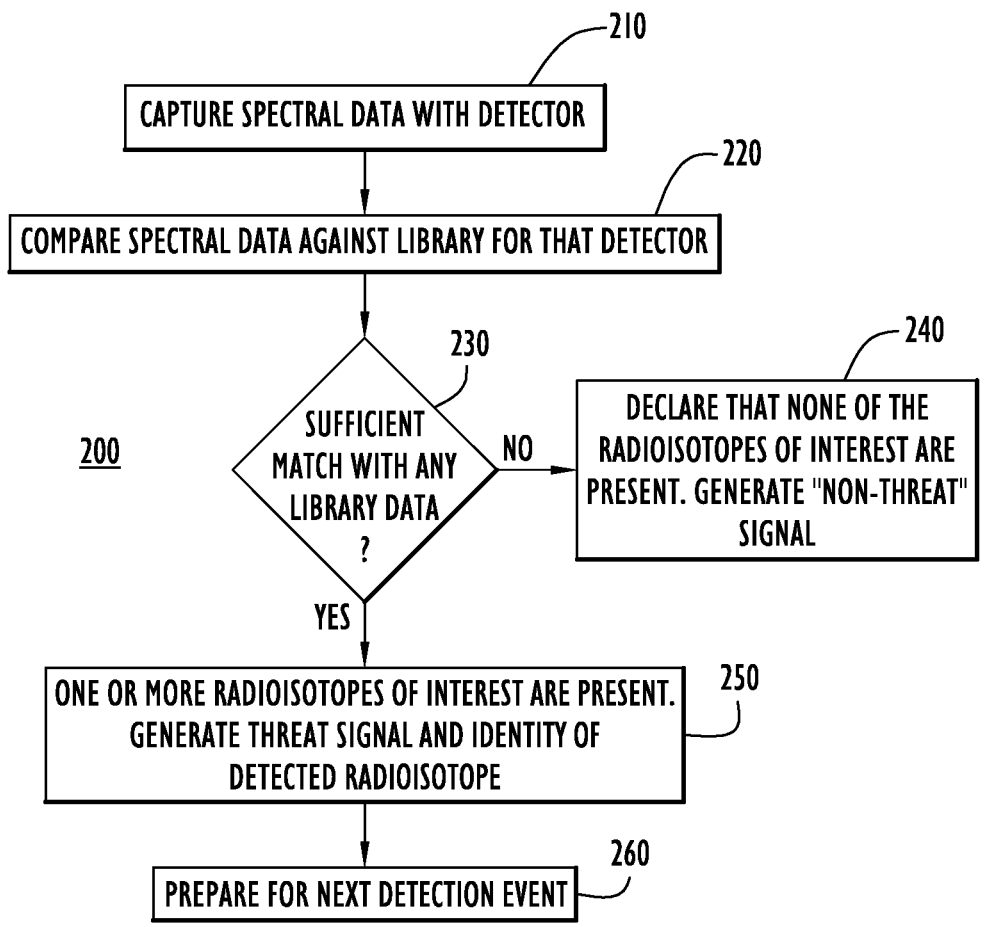
FIG. 5 is an example of a flow chart of a detection process that uses data created by the library generation process.

Turning now to FIG. 5 in conjunction with FIG. 1, an example of a process 200 is shown in which the library 60 is used. At 210, the detector 20 is activated and captures spectral data associated with a region or space 10. At 220, the computing resources 30 compare the spectra data from the detector 20 against the spectral data in the library 60. If it is determined at 230 that the spectral data from the detector 20 does not sufficiently match any of the "threat" spectral data in the library, then at 240 is declared that none of the "threat" radioisotopes of interest (considered when generating the data for the library 60) is present in the region or space. As such, a "non-threat" signal can be generated. On the other hand, if at 230 it is determined that there is a sufficient match between the spectral data from the detector 20 and the library 60 for a "threat" radioisotope, then at 250 it is declared that one or more "threat: radioisotopes of interest are present in the region or space and the identity (by textual name, chemical name or other identifier) of the one or more radioisotopes is also determined. As such, a "threat" signal is generated and the identity of the detected one or more radioisotopes is presented to a user. At 260, preparation is made for the next detection event at which 210-250 are repeated.

The techniques described herein for generating the data for the library 60 is much faster than techniques heretofore known, is much more general in that it is applicable to numerous materials and detection environments. Moreover, it is a rather quick process (several minutes) to update the library with data for a new radioisotope of interest.

Although the apparatus, system, and method are illustrated and described herein as embodied in one or more specific examples, it is nevertheless not intended to be limited to the details shown, since various modifications and structural changes may be made therein without departing from the scope of the apparatus, system, and method and within the scope and range of equivalents of the claims. Accordingly, it is appropriate that the appended claims be construed broadly and in a manner consistent with the scope of the apparatus, system, and method, as set forth in the following claims.

What is claimed is:

1. A method for determining and indicating the presence of a radioisotope threat, the method comprising:
    at a computer device, receiving spectral data associated with a region or space captured by a detector for detecting radioisotopes;
    adjusting the captured spectral data by quantum efficiency values of a quantum efficiency value matrix based on the detector;
    comparing the adjusted spectral data with library stored spectral data, the library stored spectral data being created by:
        grouping possible materials with which a radioisotope interacts into one of a plurality of material groups;
        subdividing each of the plurality of material groups into a plurality of subgroups based on atomic number and/or electron affinity of a material;
        generating first data for each of the subgroups of each of the plurality of material groups, wherein the first data comprises a plurality of values each represents an interaction between a selected representative material for a corresponding subgroup and radiation at one of a plurality of energy levels;
        generating second data representing spectral characteristics of each radioisotope of interest at the plurality of energy levels; and
        for each radioisotope of interest, computing spectrum data representing an interaction between the radioisotope of interest using the second data with the first data for each of the plurality of subgroups in each material group to create library stored spectral data to be stored in a library; and
    based on the comparison, generating either a signal indicating a threat or generating a signal indicating a non-threat.

2. The method of claim 1, wherein computing the spectrum data further comprises computing interaction between the second data for each radioisotope of interest and the first data for one or more combinations of the plurality of subgroups.

3. The method of claim 1, wherein adjusting the captured spectral data further comprises adjusting the captured spectral data for resolution of the detector.

4. The method of claim 1, wherein generating the first data further comprises generating data for a matrix for each subgroup in a material group, wherein the matrix represents an interaction between radiation and a material that is grouped into that subgroup at the plurality of energy levels.

5. The method of claim 4, wherein generating the data for the matrix for each subgroup in a material group further comprises generating a matrix M, where $$M = \begin{bmatrix} E_{1,1} & E_{1,2} & E_{i,j} & \ldots & E_{1,n} \\ E_{2,1} & E_{2,2} & & \ldots & E_{2,n} \\ \ldots & & & & \ldots \\ \ldots & & & \ldots & E_{n,n} \end{bmatrix},$$

in which $E_{i,j}$ represents the Monte Carlo Neutron and Photon (MCNP)-calculated value at an "$i^{th}$" row representing one of the energy levels and a "$j^{th}$" column representing a representative material in one of the subgroups, wherein the MCNP calculated value results from transport of a mono-energetic source of energy $E_i$ through the material.

6. The method of claim 5, wherein generating the second data comprises generating data for a vector $\vec{\beta}$ for each radioisotope of interest that represents a spectrum of radioisotope of interest in a vacuum, where $$\vec{\beta} = \begin{bmatrix} a_1 \\ a_2 \\ \ldots \\ a_n \end{bmatrix},$$

and $a_1, a_2, \ldots, a_n$ are spectrum amplitude in energy bins $E_1, \ldots E_n$, respectively.

7. The method of claim 6, wherein computing the spectrum data further comprises computing $P = M\vec{\beta}$ where P is the spectrum data.

8. The method of claim 7, wherein computing the spectrum data further comprises computing the spectrum data for the interaction of a material of a density ρ and a thickness r as $P = M^\Gamma \vec{\beta}$, where $\Gamma = \alpha\rho r$, and α is a non-negative integer.

9. The method of claim 8, wherein computing the spectrum data further comprises computing interaction between a single radioisotope and each of the subgroups comprises computing $$P = \prod_{j \in \kappa} M_j^{\Gamma_j} \vec{\beta},$$

where κ is a set material matrices $M_j$ for all of the subgroups j across all the material groups.

10. The method of claim 9, wherein computing the spectrum data further comprises computing interaction between a plurality of radioisotopes of interest and each of the subgroups comprises computing $$P = \sum_{i=1}^{J} \delta_i \prod_{j \in \kappa} M_j^{\Gamma_j} \vec{\beta}_i,$$

where $\delta_i$ is a weighted fraction of the radiation by each of the individual J radioisotope of interest represented $\vec{\beta}_i$.

11. The method of claim 1, further comprising identifying the radioisotope of interest by name or other identifier when a signal indicating a threat is generated.

12. One or more non-transitory processor-readable media encoded with instructions to determine and indicate presence of a radioisotope threat that, when executed by a processor, cause the processor to:
receive spectral data associated with a region or space captured by a detector for detecting radioisotopes;
adjust the captured spectral data by quantum efficiency values of a quantum efficiency value matrix based on the detector;
compare the adjusted spectral data with library stored spectral data, the library stored spectral data being created by:
grouping possible materials with which a radioisotope interacts into one of a plurality of material groups;
subdividing each of the plurality of material groups into a plurality of subgroups based on atomic number and/or electron affinity of a material;
generating first data for each of the subgroups of each of the plurality of material groups, wherein the first data comprises a plurality of values each represents an interaction between a selected representative material for a corresponding subgroup and radiation at one of a plurality of energy levels;
generating second data representing spectral characteristics of each radioisotope of interest at the plurality of energy levels; and
for each radioisotope of interest, computing spectrum data representing an interaction between the radioisotope of interest using the second data with the first data for each of the plurality of subgroups in each material group to create library stored spectral data to be stored in a library; and
based on the comparison, generate either a signal indicating a threat or generating a signal indicating a non-threat.

13. The one or more non-transitory processor-readable media of claim 12, wherein instructions for computing the spectrum data comprises instructions for computing interaction between the second data for each radioisotope of interest and the first data for one or more combinations of the plurality of subgroups.

14. The one or more non-transitory processor-readable media of claim 12, wherein instructions for adjusting the captured spectral data further comprises adjusting the captured spectral data for resolution of the detector.

15. The one or more non-transitory processor-readable media of claim 12, wherein instructions for generating the first data comprises instructions for generating a matrix for each subgroup in a material group, wherein the matrix represents an interaction between radiation and a material that is grouped into that subgroup at the plurality of energy levels.

16. The one or more non-transitory processor-readable media of claim 15, wherein instructions for generating the matrix for each subgroup in a material group further comprises instruction for generating a matrix M, where $$M = \begin{bmatrix} E_{1,1} & E_{1,2} & E_{i,j} \ldots & E_{1,n} \\ E_{2,1} & E_{2,2} & \ldots & E_{2,n} \\ \ldots & & & \ldots \\ \ldots & & \ldots & E_{n,n} \end{bmatrix},$$

in which $E_{i,j}$ represents the Monte Carlo Neutron and Photon (MCNP)-calculated value at an "$i^{th}$" row representing one of the energy levels and a "$j^{th}$" column representing a representative material in one of the subgroups, wherein the MCNP calculated value results from transport of a mono-energetic source of energy $E_i$ through the material.

17. The one or more non-transitory processor-readable media of claim 16, wherein instructions for generating the second data further comprises instructions for generating data for a vector $\vec{\beta}$ for each radioisotope of interest that represents a spectrum of radioisotope of interest in a vacuum, where $$\vec{\beta} = \begin{bmatrix} a_1 \\ a_2 \\ \ldots \\ a_n \end{bmatrix},$$

and $a_1, a_2, \ldots, a_n$ are spectrum amplitude in energy bins $E_1, \ldots E_n$, respectively.

18. The one or more non-transitory processor-readable media of claim 17, wherein instructions for computing the spectrum data further comprises instructions for computing $P = M\vec{\beta}$ where P is the spectrum data.

19. The one or more non-transitory processor-readable media of claim 18, wherein the logic for computing the spectrum data further comprises instructions for computing the spectrum data for the interaction of a material of a density ρ and a thickness r as $P = M^\Gamma \vec{\beta}$, where $\Gamma = \alpha \rho r$, and α is a non-negative integer.

20. The one or more non-transitory processor-readable media of claim 19, wherein instructions for computing the spectrum data further comprises instructions for computing interaction between a plurality of radioisotopes of interest and each of the subgroups comprises computing $$P = \sum_{i=1}^{J} \delta_i \prod_{j \in K} M_j^{\Gamma_j} \vec{\beta}_i,$$

where $\delta_i$ is a weighted fraction of the radiation by each of the individual J radioisotope of interest represented $\vec{\beta}_i$.

21. A system for determining and indicating the presence of a radioisotope threat, comprising:
a memory storing computer executable instructions; and
a computer processor coupled to the memory and configured to execute the computer executable instructions to:
 adjust the captured spectral data by quantum efficiency values of a quantum efficiency value matrix based on the detector;
 compare the adjusted spectral data with library stored spectral data, the library stored spectral data being created by:
  grouping possible materials with which a radioisotope interacts into one of a plurality of material groups;
  subdividing each of the plurality of material groups into a plurality of subgroups based on atomic number and/or electron affinity of a material;
  generating first data for each of the subgroups of each of the plurality of material groups, wherein the first data comprises a plurality of values each represents an interaction between a selected representative material for a corresponding subgroup and radiation at one of a plurality of energy levels;
  generating second data representing spectral characteristics of each radioisotope of interest at the plurality of energy levels; and
  for each radioisotope of interest, computing spectrum data representing an interaction between the radioisotope of interest using the second data with the first data for each of the plurality of subgroups in each material group to create library stored spectral data to be stored in a library; and
 based on the comparison, generate either a signal indicating a threat or generating a signal indicating a non-threat.

22. The system of claim 21, wherein computing the spectrum data further comprises computing interaction between the second data for each radioisotope of interest and the first data for one or more combinations of the plurality of subgroups.

23. The system of claim 21, wherein to adjust the captured spectral data further comprises to adjust the captured spectral data for resolution of the detector.

24. The system of claim 21, wherein generating the first data further comprises generating data for a matrix for each subgroup in a material group, wherein the matrix represents an interaction between radiation and a material that is grouped into that subgroup at the plurality of energy levels.

25. The system of claim 24, wherein generating the data for the matrix for each subgroup in a material group further comprises generating a matrix M, where $$M = \begin{bmatrix} E_{1,1} & E_{1,2} & E_{i,j} & \ldots & E_{1,n} \\ E_{2,1} & E_{2,2} & & \ldots & E_{2,n} \\ \ldots & & & & \ldots \\ \ldots & & & \ldots & E_{n,n} \end{bmatrix},$$

in which $E_{i,j}$ represents the Monte Carlo Neutron and Photon (MCNP)-calculated value at an "$i^{th}$" row representing one of the energy levels and a "$j^{th}$" column representing a representative material in one of the subgroups, wherein the MCNP calculated value results from transport of a mono-energetic source of energy $E_i$ through the material.

* * * * *